US005306624A

United States Patent [19]

Roelant

[11] Patent Number: 5,306,624
[45] Date of Patent: Apr. 26, 1994

[54] PROCESS OF QUANTIFYING CELL NUMBER

[75] Inventor: Chris Roelant, Wilsele, Belgium

[73] Assignee: Packard Instrument Co., Inc., Meriden, Conn.

[21] Appl. No.: 946,974

[22] Filed: Sep. 17, 1992

[51] Int. Cl.⁵ .................. C12Q 1/06; G01N 21/76
[52] U.S. Cl. ................................. 435/39; 435/4;
435/25; 435/28; 435/29; 435/34; 435/89;
435/968; 435/975; 436/172; 436/904; 436/905;
422/52
[58] Field of Search ............... 435/39, 4, 25, 28, 29,
435/34, 89, 968, 975; 436/172, 904, 905; 422/52

[56] References Cited

U.S. PATENT DOCUMENTS 5,093,238  3/1992  Yamashoji et al. .................. 435/29
5,171,668  12/1992  Sugiyama et al. .................. 435/25

OTHER PUBLICATIONS

Yamashoji et al., *Analytical Biochemistry*, vol. 181, pp. 149-152, 1989.
Kohen et al., *Alternative Immunoassays*, Edited by W. P. Collins, 1985, John Wiley & Sons, Ltd., Chapter 8, pp. 103-121.
Kricka, *Clin. Chem.*, vol. 37, No. 9, pp. 1472-1481, 1991.
Minkenberg et al., *Journal of Immunological Methods*, vol. 71, pp. 66-67, 1984.
Oh et al., *Chemical Abstracts*, vol. 114, p. 425, Ref. #181815k, 1991.
Weeks et al., *Methods in Enzymology*, vol. 133, pp. 366-387, 1986.
Yamashoji et al., *Analytical Biochemistry*, vol. 207, pp. 255-260, 1992.
Porter et al., *Journal of Immunological Methods*, vol. 155, pp. 151-157, 1992.
Furnikawa et al., *Scand. J. Immunol.*, vol. 35, pp. 561-567, 1992.
Yamashoji et al., *Biochimica et Biophysica Acta*, vol. 1059, pp. 99-105, 1991.
Miyake et al., *Chemical Abstracts*, vol. 114, Ref. No. 183079x, 1991.
Mosmann, T., J. Immunol. Metho. (1983) 65:55-63.
Molecular Probes, Inc. (1992) pp. 145-148.
Riss, T., Promega Notes (Aug. 1991) 32:1-4.

*Primary Examiner*—Michael G. Wityshyn
*Assistant Examiner*—Abdel A. Mohamed
*Attorney, Agent, or Firm*—Arnold, White & Durkee

[57] ABSTRACT

The present invention provides a process of quantifying the number of viable cells in an aqueous suspension of cells using an energy-emitting non-hazardous probe and a probe-trigger. The process provides quantification data in short periods of time without the use of hazardous materials. A process of the present invention can also be used to quantify negatively charged particle number, assay for cytotoxicity, assay for cell proliferation and assay for cell differentiation. Still further, the present invention provides an assay kit for quantification of cells or negatively charged particles.

47 Claims, 8 Drawing Sheets

PROCESS OF QUANTIFYING CELL NUMBER

Technical Field of the Invention

The present invention relates to a process of quantifying cell number using an energy-emitting non-hazardous probe. This invention also relates to a cell toxicity, cell proliferation and cell differentiation assay.

BACKGROUND OF THE INVENTION

Typically, cell number is determined, directly, by microscopic or electronic enumeration, or indirectly, by the use of chromogenic dyes, incorporation of radioactive precursors or measurement of metabolic activity of cellular enzymes. These methods are often insensitive, labor intensive, or hazardous ($^3$H-thymidine incorporation).

A recent colorimetric assay is based on the cellular conversion of a tetrazolium salt into a blue formazan product that is detected using a ELISA plate reader. (Mossmann T., *J. Immunol, Meth.* 65:55–63 (1983)

Despite numerous attempts to reduce several technical problems related to this method (e.g., protein precipitation and incomplete solubilization of the formazan product), the assay is still time consuming (4 hours incubation at 37° C.) and still requires the use of highly toxic materials (e.g., dimethyl formamide and thiazoyl blue).

BRIEF SUMMARY OF THE INVENTION

In one aspect, the present invention contemplates a process of quantifying the number of viable cells in an aqueous suspension of cells, which process comprises the steps of:
a) admixing an effective detection amount of an energy-emitting nonhazardous probe with the suspension to form an admixture, wherein the emission of energy from the probe is proportional to and activated by a stimulant;
b) exposing the admixture to an effective triggering amount of a probe-trigger, wherein the probe-trigger interacts with the viable cells in the suspension to generate the stimulant in an amount proportional to the number of the viable cells;
c) maintaining the admixture under physiological reaction conditions and for a period of time sufficient for activation of the energy-emitting nonhazardous probe; and
d) detecting the emission of energy from the probe.

In a preferred embodiment, the energy-emitting non-hazardous probe is a light-emitting non-hazardous probe such as a chemiluminogenic probe or an otherwise luminescent probe. A preferred chemiluminogenic probe is lucigenin, lophine, luminol, a dioxetane or acridinium ester.

A stimulant is preferably an unstable oxygen derived species such as singlet oxygen, superoxide radical, a hydroxyl radical, hydrogen peroxide or a protonated superoxide radical.

A probe-trigger used in a process of the present invention is preferably a reduced form of a coenzyme for an oxidation-reduction reaction. Exemplary and preferred such probe-triggers are NADH, NADPH, FMNH and FADH. Viable cells that can be quantified using a process of the present invention include living and freeze-dried cells. Those cells can be suspended in an aqueous suspension comprising water or a mixture of an organic solvent and water. Preferably, the organic solvent is acetone.

Where the energy-emitting probe is cationic, a quantification assay of the present invention can be used to quantify the number of negatively charged particles in an aqueous suspension of particles.

In another aspect, the present invention contemplates a cell toxicity assay comprising the steps of:
a) providing an aqueous suspension of cells to be tested;
b) admixing an effective detection amount of an energy-emitting non-hazardous probe with the suspension to form an admixture, wherein the emission of energy from the probe is proportional to and activated by a stimulant;
c) exposing the admixture to a first effective triggering amount of a first probe-trigger, wherein the first probe-trigger interacts with viable cells in the suspension to generate the stimulant in an amount proportional to the number of viable cells;
d) maintaining the admixture under physiological reaction conditions and for a period of time sufficient for activation of the energy-emitting non-hazardous probe;
e) detecting the emission of energy from the chemiluminogenic probe;
f) contacting the admixture to a suspected toxin;
g) re-exposing the admixture to a second effective triggering amount of a second probe-trigger, wherein the second probe-trigger interacts with viable cells to generate the stimulant in an amount proportional to the number of viable cells;
h) maintaining the admixture under physiological reaction conditions and for a period of time sufficient for activation of the energy-emitting non-hazardous probe;
i) detecting the emission of energy from the probe; and
j) comparing the detected emission of energy from step (e) with the detected energy from step (i) and thereby the effect of the suspected toxin.

An energy-emitting probe, a probe-trigger and a stimulant used in accordance with that assay are the same as set forth above for a cell quantification assay. In a preferred embodiment, the first and second probe trigger are the same.

The present invention also contemplates a cell proliferation and a cell differentiation assay that each comprises steps similar to that of a cell toxicity assay above.

In yet another aspect, the present invention contemplates an assay kit for quantifying cell number comprising a first container containing an energy-emitting non-hazardous probe in an amount sufficient to perform at least one cell quantification assay, wherein the emission of energy from the probe is proportional to and activated by a stimulant. The assay kit can further comprise a second container containing a probe-trigger in an amount sufficient to perform at least one cell quantification assay, wherein the probe-trigger interacts with viable cells to generate the stimulant in an amount proportional to the number of viable cells.

BRIEF DESCRIPTION OF THE DRAWINGS

In the drawings, which form a portion of the specification.

DETAILED DESCRIPTION OF THE INVENTION

I. A Process for Quantifying Cells

Figure 1:
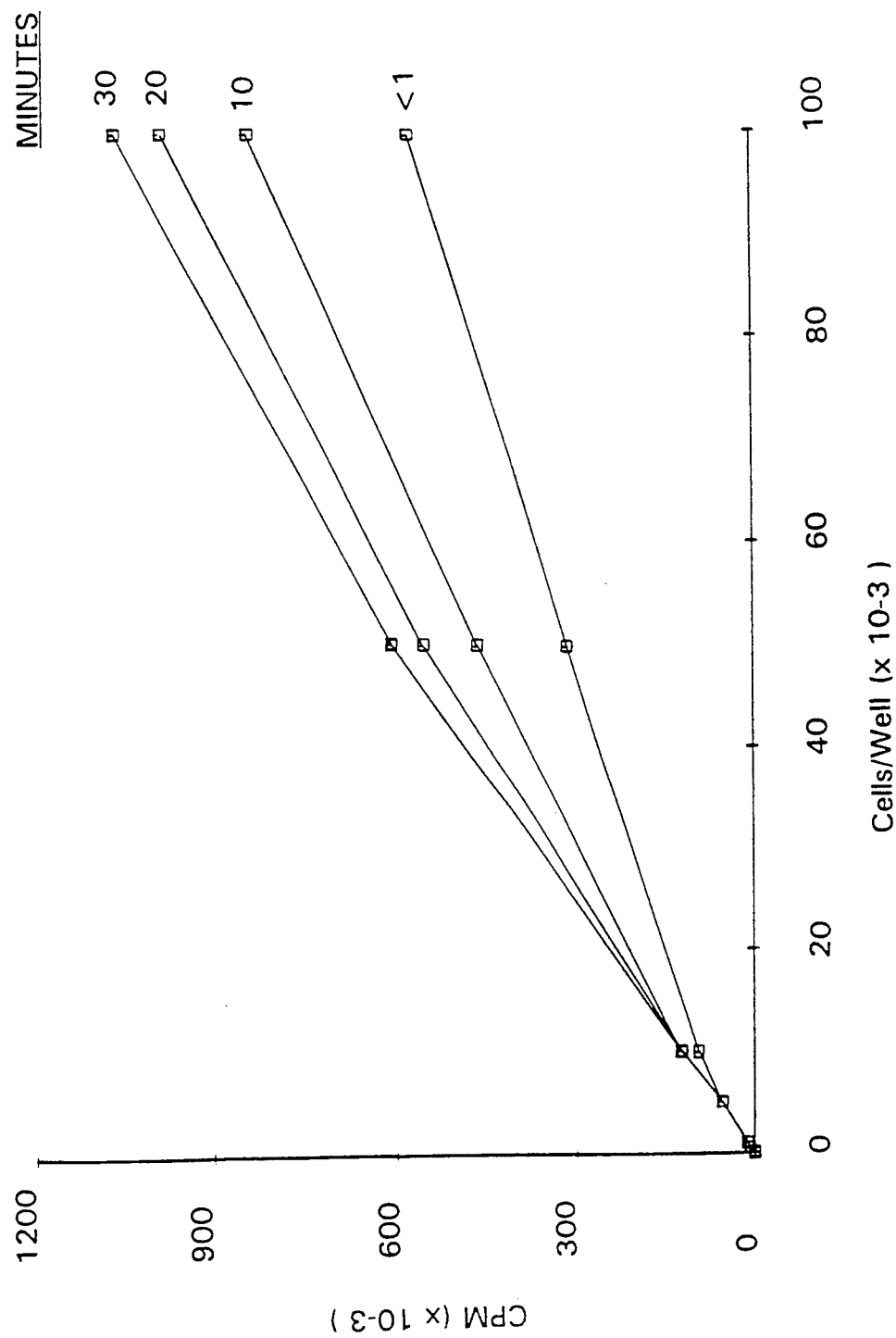
FIG. 1 shows chemiluminescence (CPM) as a function of cell number immediately (<1), 10 minutes, 20 minutes and 30 minutes after the addition of a probe, probe-trigger solution.

In one aspect, the present invention provides a process of quantifying the number of viable cells in an aqueous suspension of cells. In accordance with that process, an effective detection amount of an energy-emitting non-hazardous probe is admixed with a suspension of cells to form an admixture, wherein the emission of energy from the probe is proportional to and activated by a stimulant. The admixture is exposed to an effective triggering amount of a probe-trigger, wherein the probe-trigger interacts with viable cells in the admixture to generate the stimulant in an amount proportional to the number of viable cells.

The admixture is then maintained under physiological reaction conditions and for a period of time sufficient for activation of the energy-emitting non-hazardous probe. The emission of energy from the probe is then detected.

As used herein, the phrase "energy-emitting non-hazardous probe" means a compound that gives off energy in the form of heat, electromagnetic fields or radiation (e.g., photons, electrons, neutrons and the like). The emission of energy from such a probe is stimulated by and proportional to another compound referred to herein as a "stimulant". An energy-emitting probe used in a process of the present invention, at the levels used in that process, is non-hazardous to humans as well as to the cells being counted. Non-hazardous includes non-toxic, non-carcinogenic and non-pathogenic.

In a preferred embodiment, an energy-emitting probe is a light-emitting probe (i.e., the emitted energy is radiant energy in the form of light). Even more preferably, the light-emitting probe is a luminescent probe such as a chemiluminogenic or fluorescent probe.

Exemplary and preferred chemiluminogenic probes are bis-N-methylacridinium nitrate (lucigenin), 2,4,5-triphenylimidazole (lophine), 5-amino-2,3-dihydro-1,4-phthalazinedione (luminol), a dioxetane or acridinium ester.

Preferably, a fluorescent probe is a cationic membrane probe such as a carbocyanine or a pyrene. Exemplary and preferred fluorescent probes include 1,1'-dihexadecyloxacarbocyanine, 3,3'-dioctadecyloxacarbocyanine, 1,1'-didodecyl-3,3,3',3'-tetramethylindocarbocyanine, 1,1'-dihexadecyl-3,3,3',3'-tetramethylindocarbocyanine, 1,1'-dioctadecyl-3,3,3',3'-tetramethylindocarbocyanine, 1,1'-dioctadecyl 3,3,3',3'tetramethylindodicarbocyanine, 1,1'-didocosanyl-3,3,3',3'-tetramethylindocarbocyanine, 3,3'-dioctadecylthiocarbocyanine, octadecyl rhodamine B, rhodamine 6G-octadecyl ester, rhodamine 101-octadecyl ester, 1-pyrenemethyltrimethylammonium iodide and 1-pyrenebutyltrimethylammonium bromide. Fluorescent and chemiluminogenic probes are commercially available (e.g., Molecular Probes, Inc., Eugene, Oreg.; Aldrich Chemical Co., Inc., Sigma Chemical Co., Inc., St. Louis, Mont.).

In accordance with a process of the present invention, an effective detection amount of an energy-emitting probe is admixed with a suspension of cells. As used herein, "an effective detection amount" is that amount of a probe needed to provide detectable energy levels in proportion to the number of cells to be counted. An effective detection amount varies inter alia with the number of cells and the nature of the probe. Means for determining an effective detection amount for a given probe are well known in the art.

Where the number of cells to be counted is from 0 to about $10^{10}$ cells/milliliter (ml) and the probe is a chemiluminogenic probe, an effective detection amount is from about $10^{-3}$M to about $10^{-3}$M.

A "stimulant" as used herein means anything that stimulates the emission of energy from an energy-emitting probe in proportion to the level of that stimulant. A stimulant can be a chemical substance such as a molecular or ion, or a source of energy. By way of example, a fluorescent probe is stimulated to emit light of a given wavelength in response to energy stimulation (decay of the fluorescent probe from a higher to a lower electronic state). In the case of a fluorescent probe, the stimulant is an inherent feature of the probe and not a separate entity. By way of further example, where the energy-emitting probe is a chemiluminogenic probe, a stimulant is an unstable oxygen derived species such as singlet oxygen, superoxide radical, a hydroxyl radical, hydrogen peroxide or a protonated superoxide radical.

As used herein, a "probe-trigger" is anything that, upon exposure to an admixture comprising viable cells and an energy-emitting probe, interacts with those cells so as to generate a stimulant in proportion to the number of viable cells in the admixture and which stimulant proportionately stimulates emission of energy from that probe.

A probe trigger used in a process of the present invention can be a chemical compound such as an enzyme cofactor, a metabolite of the viable cells being counted (e.g. an enzyme cofactor), an integral component of the viable cells being counted (e.g., a cell surface receptor) or an energy source such as light (e.g., the excitation wavelength of a fluorescent probe).

Where the probe is a chemiluminogenic probe and the stimulant is an unstable oxygen derived species, a preferred probe-trigger is a reduced form of a coenzyme for an oxidation-reduction reaction. Exemplary and preferred such probe-triggers are reduced nicotinamide adenine dinucleotide (NADH), reduced nicotinamide adenine dinucleotide phosphate (NADPH), reduced flavin mononucleotide (FMNH) or reduced flavin adenine dinucleotide (FADH).

An admixture containing cells to be counted and an energy-emitting probe is exposed to an effective triggering amount of a probe-trigger. An "effective triggering amount" is that amount of a probe-trigger needed to generate sufficient stimulant to stimulate detectable emitted energy levels.

An effective triggering amount depends predominantly upon the nature of the probe-trigger, the nature of the stimulant, the nature of the energy-emitting probe and the number of cells to be counted. Means for determining an effective triggering amount are well known and readily apparent to one of skill in the art. A suspension of cells can be exposed to a probe-trigger simultaneously with or after admixing with an energy-emitting probe.

Once the cell suspension has been admixed with an energy-emitting probe and exposed to a probe trigger, the admixture is maintained for a time period and under physiological reaction conditions sufficient for the probe-trigger to interact with viable cells in the admixture and generate a stimulant that stimulates energy emission from the energy-emitting probe.

Biological reaction conditions include temperature, pH value, osmolality, tonicity and the like. Typically, temperature can range from about 10° C. to about 50° C. and, preferably from about 20° C. to about 40° C. pH can range from a value of about 6.0 to a value of about 8.5 and, preferably from a value of about 6.5 to a value of about 7.5. Admixture osmolality can range from about 200 milliosmols per liter (mOsm) to about 500 mOsm and, preferably from about 250 mOsm to about 350 mOsm. Admixture tonicity is preferably isotonic to the cells being counted.

The only limitation on physiological reaction conditions is that the conditions used not adversely affect cell viability, interaction of the probe-trigger with viable cells, generation of a stimulant, stimulation of energy emission or detection of emitted energy. Means for determining suitable physiological reaction conditions are readily apparent and well known to one of skill in the art.

Maintenance time depends predominantly upon the biological reaction conditions, and the particular characteristics of a given probe-trigger, stimulant and energy-emitting probe. Preferably, maintenance time is less than about 60 minutes. More preferably, maintenance time is less than about 30 minutes and, even more preferably less than about 10 minutes. Where cells are quantified using a chemiluminogenic probe, emitted energy was detectable immediately after exposing those cells to NADH (see Example 1, hereinafter).

A quantification process of the present invention has use for quantifying viable cells in an aqueous suspension of cells. As used herein, "viable" means cells whose structure and function are intact. Viable cells include fresh cells isolated from a living organism, cells grown or cultured in vitro, or cells reconstituted from frozen or freeze-dried preparations.

Cells to be counted are suspended in an aqueous medium having an osmolality, tonicity, pH value and ionic composition that supports and maintains cell viability. Exemplary media include normal saline, Ringer's solutions and commercially available cell culture media such as minimum essential medium (MEM), RPMI, Dulbecco's and Eagle's medium.

Where a chemiluminogenic probe is used to quantify cell number, the aqueous medium may further comprise an organic solvent that has a stabilizing effect on the formation of superoxide. A preferred such organic solvent is acetone. A preferred acetone concentration in such an aqueous medium is from about 20 volumes percent to about 60 volumes percent.

II. A Process for Quantifying Negatively Charged Particles

In another aspect, the present invention provides a process of quantifying the number of negatively charged particles in an aqueous suspension of particles. In accordance with that process, an effective detection amount of a cationic (positively charged) energy-emitting non-hazardous probe is admixed with a suspension of particles to form an admixture, wherein the emission of energy from the probe is proportional to and activated by a stimulant. The admixture is exposed to an effective triggering amount of a probe-trigger, wherein the probe-trigger interacts with negatively charged particles in the admixture to generate the stimulant in an amount proportional to the number of negatively charged particles.

The admixture is then maintained under reaction conditions and for a period of time sufficient for activation of the energy-emitting non-hazardous probe. The emission of energy from the probe is then detected.

An energy-emitting probe and a probe-trigger that can be used in accordance with a particle quantification process of the present invention are the same as set forth above in relation to a process for quantifying viable cell number except that the probe and probe-trigger do not depend upon a viable cell for stimulant generation and probe activation.

As used herein, a "negatively charged particle" means a particle having a net negative surface charge. Because the negatively charged particles that are quantified by a process of the present invention are not necessarily living cells, the reaction conditions used to maintain the admixture after exposure to a probe-trigger can vary from those conditions set forth above in relation to a process for quantifying viable cells.

In accordance with a process for quantifying negatively charged particles, temperature can range from about 4° C. to about 100° C. pH can range from a value of about 2.0 to a value of about 11.0 and, preferably from a value of about 4.0 to a value of about 9.0. Admixture osmolality can range from that of distilled water to about 1500 mOsm and, preferably from about 100 mOsm to about 500 mOsm.

The only limitation on reaction conditions is that the conditions used not adversely affect interaction of the probe-trigger with the negatively charged particle, generation of a stimulant, stimulation of energy emission or detection of emitted energy. Means for determining suitable reaction conditions are readily apparent and well known to one of skill in the art.

Where the probe-trigger is an oxidized or reduced form of a coenzyme for an oxidation-reduction reaction, a probe is a chemiluminogenic probe and the stimulant is an unstable oxygen derived species, a process of the present invention can be used to qualify the catalytic activity of an enzyme that provides oxidized or reduced coenzymes.

Exemplary such enzymes are alkaline phosphatases and dehydrogenases such as glucose-6-phosphate dehydrogenase or D-galactose-dehydrogenase. preferred probe-trigger for qualtification of alkaline phosphatase or dehydrogenase activity is NADH or NADPH.

A process of the present invention for quantifying cell number has application in a number of assays where it is desirable to monitor the number of viable cells. Exemplary such assays include an assay for cell toxicity, an assay for cell proliferation and an assay for celldifferentiation.

III. Cell Toxicity, Proliferation and Differentiation Assays

In another aspect, the present invention contemplates a cell toxicity assay comprising the steps of:
a) providing an aqueous suspension of cells to be tested;
b) admixing an effective detection amount of an energy-emitting non-hazardous probe with the suspension to form an admixture, wherein the emission of energy from the probe is proportional to and activated by a stimulant;
c) exposing the admixture to a first effective triggering amount of a first probe-trigger, wherein said first probe-trigger interacts with viable cells in the aqueous suspension to generate the stimulant in an amount proportional to the number of viable cells;
d) maintaining the admixture under biological reaction conditions and for a period of time sufficient for activation of the energy-emitting nonhazardous probe;
e) detecting the emission of energy from the energy-emitting probe;
f) contacting the admixture with a suspected toxin;
g) re-exposing the admixture to a second effective triggering amount of a second probe-trigger, wherein the second probe-trigger interacts with viable cells to generate the stimulant in an amount proportional to the number of viable cells;
h) maintaining the admixture under biological reaction conditions and for a period of time sufficient for activation of the energy-emitting non-hazardous probe;
i) detecting the emission of energy from the energy-emitting probe; and
j) comparing the detected emission of energy from step (e) with the detected energy from step (i) and thereby the effect of the suspected toxin.

An energy-emitting probe, a probe-trigger and a stimulant used in accordance with that assay are the same as set forth above for a cell quantification process. In a preferred embodiment, the first and second probe trigger are the same.

The present invention further contemplates assays for cell proliferation or differentiation, which processes are the same as set forth above in relation to a cell toxicity assay except that a cell proliferation stimulant or cell differentiation stimulant is substituted for the suspected toxin.

The effect of the suspected toxin is determined by comparing the detected emission of energy before (step e) and after (step i) exposure to the toxin, proliferation or differentiation stimulant.

IV. Assay Kit

In yet another aspect, the present invention contemplates an assay kit for quantifying cell number comprising a first container containing an energy-emitting non-hazardous probe in an amount sufficient to perform at least one cell quantification assay, wherein the emission of energy from the probe is proportional to and activated by a stimulant.

An energy-emitting probe in a first container of an assay kit of the present invention can have a variety of formulations. The probe can be suspended or dissolved in a suitable medium or can be in a dry form. The only limitation on the formulation is that a particular formulation provide stability to the probe such that the probe does not undergo chemical alteration during storage. Means for determining a suitable formulation for a particular energy-emitting probe are readily apparent and well known to one of ordinary skill in the art.

The assay kit can further comprise a second container that contains a probe-trigger in an amount sufficient to perform at least one cell quantification assay, wherein the probe-trigger interacts with viable cells to generate a stimulant in an amount proportional to the number of viable cells and wherein the stimulant proportionately activates the energy-emitting probe of the first container. A probe-trigger can also exist as a suspension, solution or in dry form.

By way of example, an exemplary two container kit comprises a first container containing 100 ml of $10^{-3}$M dimethyl bis acridinium nitrate (probe) in deionized water and a second container containing 100 ml of $10^{-3}$M reduced beta nicotinamide adenine dinucleotide (NADH) (probe trigger) in a 50% (V/V) deionized water acetone mixture.

If stored properly at about 4° C., those solutions remain stable for several months. To quantify cells, one can proceed by admixing from about 20 $\mu$l to about 35 $\mu$l of the probe solution with from about 100 $\mu$l to about 200 $\mu$l of an aqueous cell suspension. From about 100 $\mu$l to about 200 $\mu$l of the probe-trigger solution is added to the admixture and energy emission measured.

Where it is desirable to expose cells to an energy-emitting probe and a probe-trigger at the same time, the first and second containers can be the same container.

In a preferred embodiment, the first and second container are labelled with indicia setting forth the nature, amount or concentration and effective amounts of the ingredients contained therein.

The following examples illustrate particular embodiments of the present invention and are not limiting of the claims or specification in any way.

EXAMPLE 1

Quantification of Cell Number

A. Materials and Methods

K562 cells (leukocytes) were suspended in RPMI medium (pH 7.2 supplemented with 10% fetal calf serum and 1% penicillin-streptomycin) and plated into individual wells of a 96 well microtitler plate so that the number cells ranged from 0 cells/well to about 100,000 ($10^5$) cells/well.

An aqueous solution of bis-N-methylacridinium nitrate (lucigenin) and NADH was admixed with each suspension to form an admixture having a lucigenin concentration of about $10^{-4}$M and an NADH concentration of about $5\times10^{-4}$M. The lucigenin and NADH were obtained from Sigma Chemical Co., (St. Louis, Mont.).

The admixtures were maintained at room temperature for from 0 to about 30 minutes. Emitted energy in the form of luminescence (light) was monitored from each admixture for a period of 30 minutes following addition of lucigenin and NADH. Emitted energy was monitored with a Beckman Scintillation Counter LS7500 (Beckman Instruments). The results of those studies are summarized in FIGS. 1-8.

B. Effects of Maintenance Time

The data in FIG. 1 show that chemiluminescence can be detected immediately after exposure of viable cells to an energy-emitting probe and a probe-trigger in accordance with a process of the present invention. The data in FIG. 1 also show that emitted energy is directly proportional to cell number over the range of 0 to about 100,000 cells per well.

The data in FIG. 1 also shows that emitted energy is still proportional to cell number 10, 20 and 30 minutes, respectively, after exposure of viable cells to an energy-emitting probe and a probe-trigger.

These data show that viable cells can be quantified in accordance with a process of the present invention in a very short period of time using non-hazardous materials. The data further show that quantification information provided by such a process continues for at least 30 minutes.

C. Effect of Cell Number

K562 Cells were prepared in accordance with procedures set forth above in Example 1A, except that cell number/well ranged from 0 to about 10,000 cells/well. Emitted energy was detected 20 minutes after exposure of cells to bis-N-methylacridinium nitrate (lucigenin) and NADH. The results of those studies are summarized in FIGS. 2-5.

Figure 2:
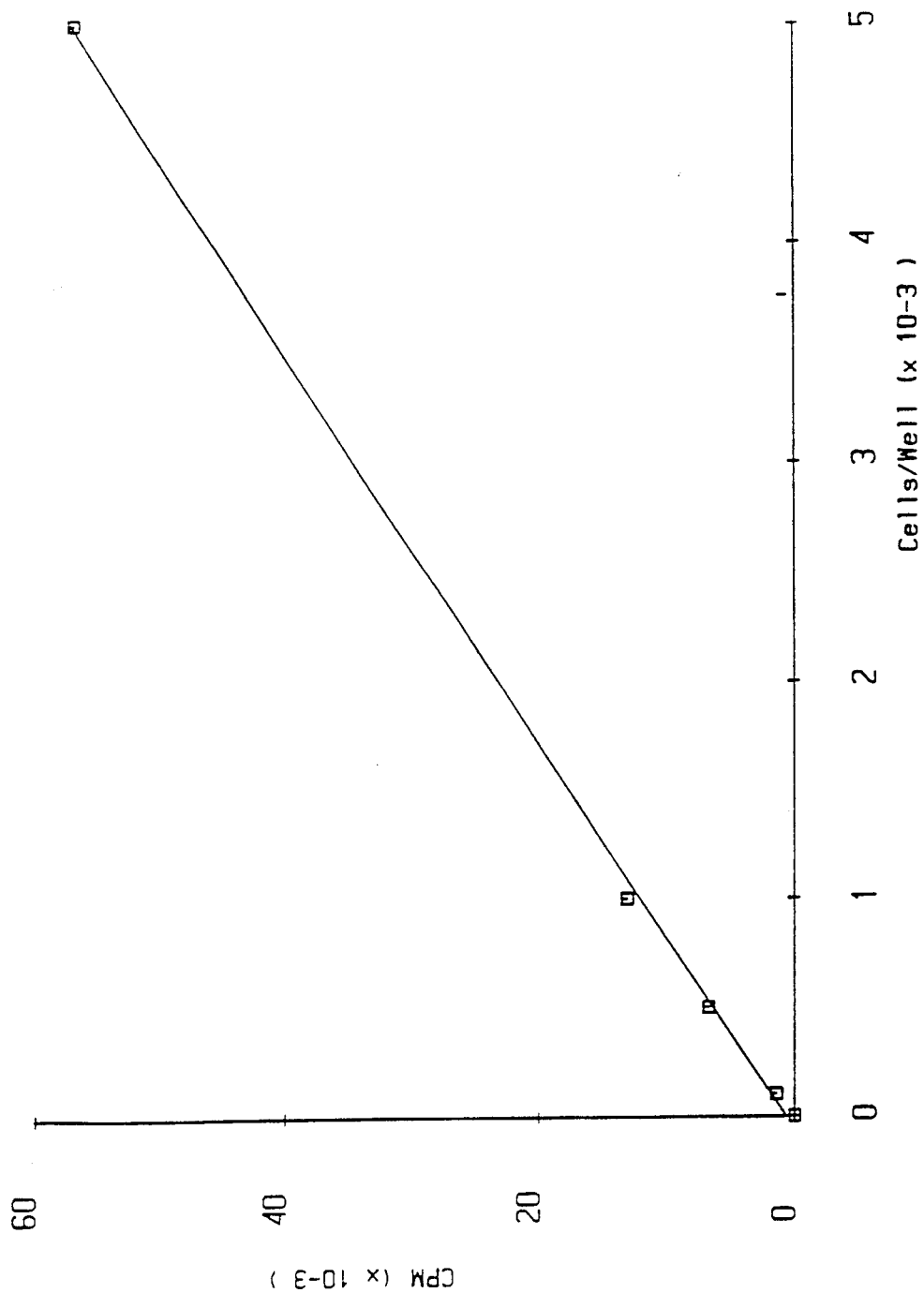
FIG. 2 shows chemiluminescence (CPM) as a function of cell number (0–5,000 cells) 20 minutes after the addition of a probe, probe-trigger solution.
Figure 3:
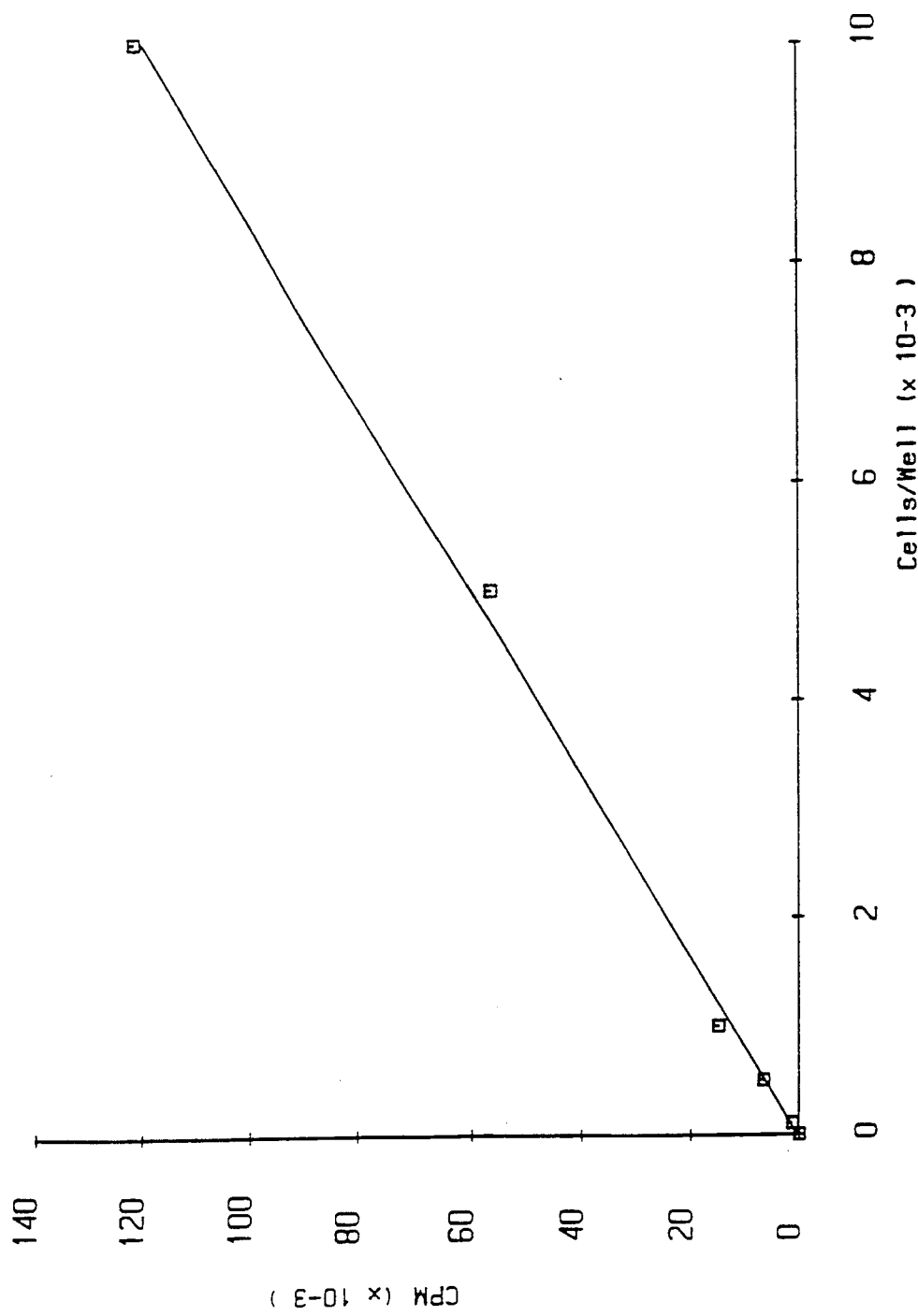
FIG. 3 shows chemiluminescence (CPM) as a function of cell number (0–1,000 cells) 20 minutes after the addition of a probe, probe-trigger solution.
Figure 4:
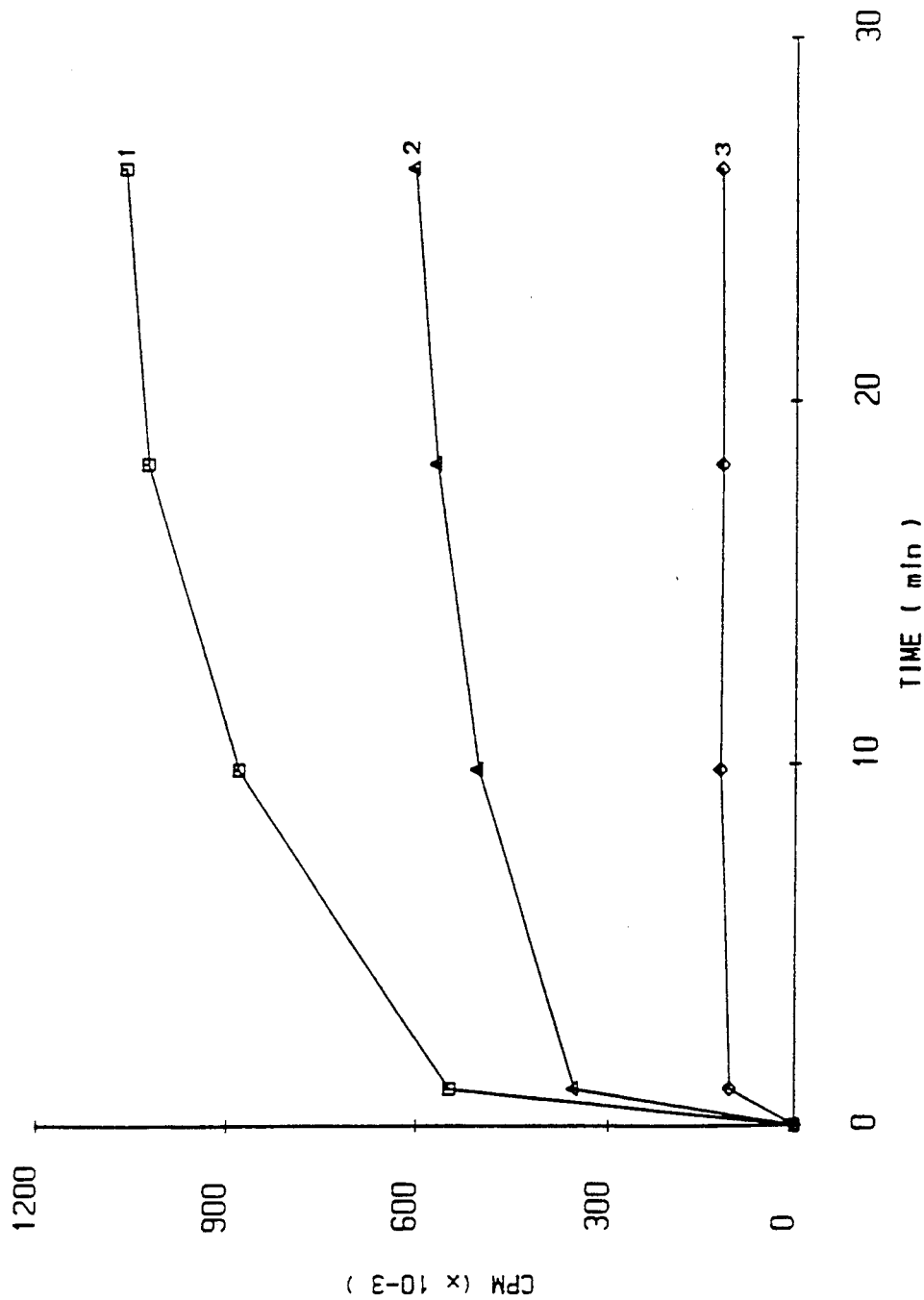
FIG. 4 shows the time kinetics of chemiluminescence (CPM) as a function of cell number (1. 100,000 cells; 2. 50,000 cells; 3. 10,000 cells) 20 minutes after the addition of a probe, probe-trigger solution.
Figure 5:
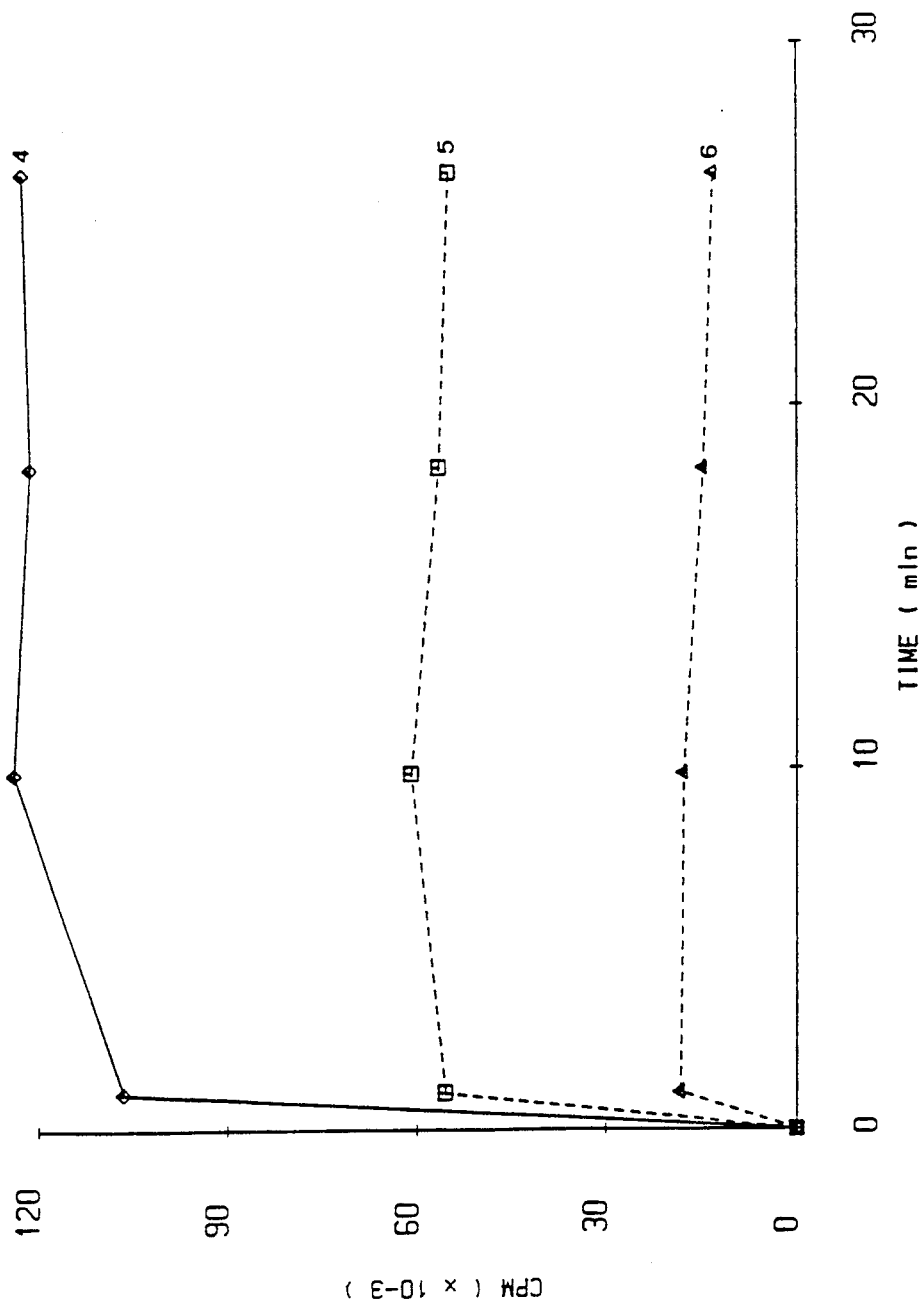
FIG. 5 shows the time kinetics of the chemiluminescence (CPM) as a function of cell number (4. 10,000 cells; 5. 5,000 cells; 6. 1,000 cells) 20 minutes after the addition of a probe, probe-trigger solution.

The data in FIGS. 2 and 3 show that a process of the present invention can be used to quantify cell numbers as low as about 100 cells/well. The data in FIGS. 4 and 5 show that energy emission is stable over a time period of about 30 minutes.

EXAMPLE 2

Studies with Whole Blood

Whole blood was collected via venipuncture from normal patients and patients suffering from leukopenia (reduced number of leukocytes) into syringes containing anticoagulant (EDTA). An aliquot of whole blood was heated at a temperature of about 56° C. for about 30 minutes. About 20μl aliquots of normal (Group 1), leukopenic (Groups 2 and 3) and heat treated (Group 4) blood were plated into individual wells of a 96 well microtiter plate.

Each well was admixed with bis-N-methylacridinium nitrate (lucigenin) and NADH in accordance with the procedures of Example 1 and maintained at about room temperature for from 0 to about 80 minutes. Emitted energy was detected in accordance with the procedures of Example 1. The results of those studies are summarized in FIG. 6.

Figure 6:
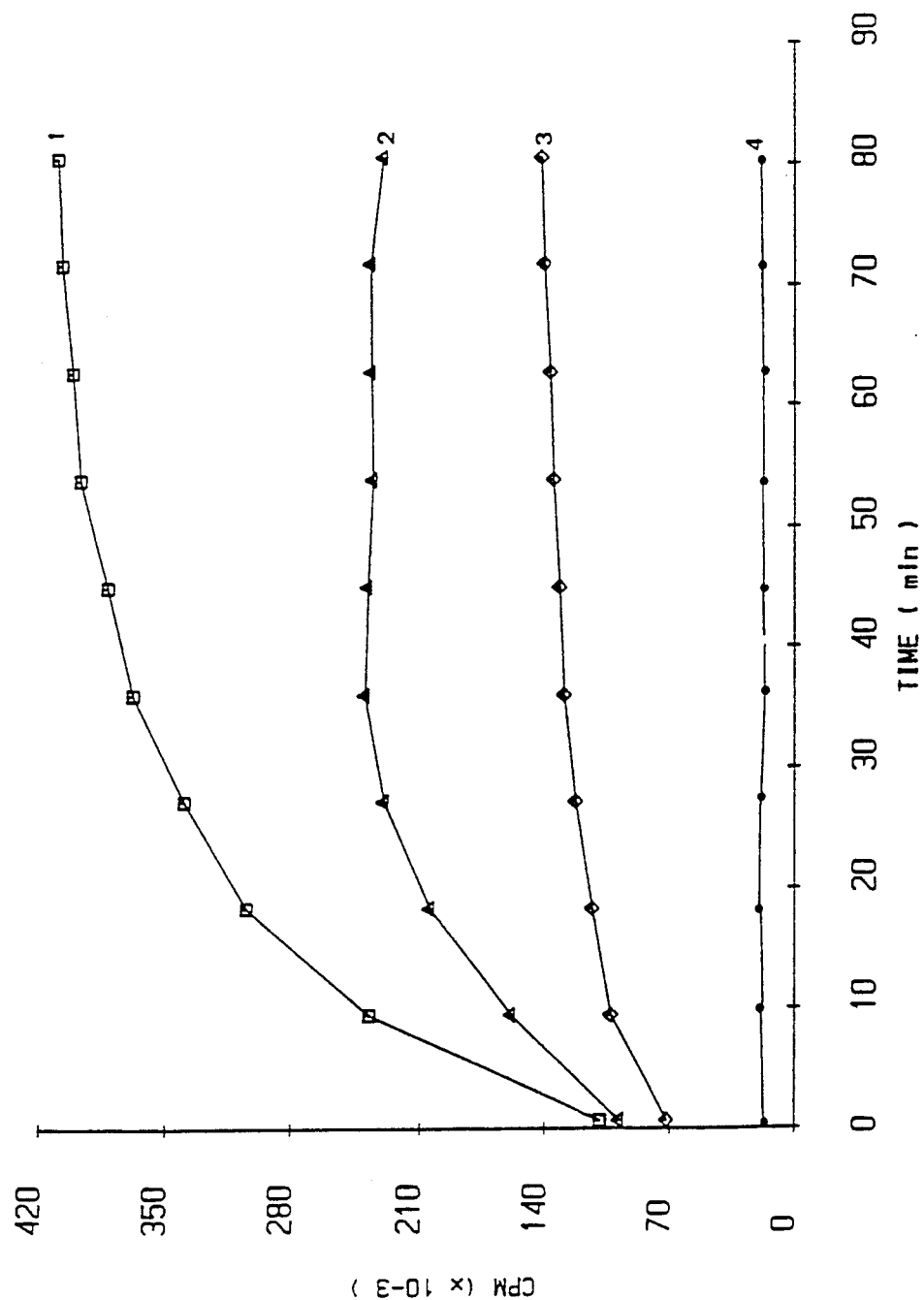
FIG. 6 shows the kinetics of the chemiluminescence (CPM) of whole blood as a function of cell number from 0 to 80 minutes after the addition of a probe, probe-trigger solution. Group 1, normal blood sample; Groups 2 and 3, leukopenic blood samples; Group 4, heat treated normal blood.

The data in FIG. 6 show that viable cells in whole blood can be quantified in accordance with a process of the present invention. A process of the present invention can, thus, be seen to have advantages over other means of cell counting that employ colorimetric procedures that likely are affected by chromophores in whole blood.

EXAMPLE 3

Cell Toxicity Assay

K562 Cells were prepared in accordance with the procedures of Example 1, above. Various concentrations of Triton X-100 (Sigma Chemical Co.) were added to aliquots of the cells containing about 50,000 cells. Triton X-100 is a cytotoxic detergent known to disrupt cell membranes and kill cells. After about five minutes, Triton X-100 treated cells were exposed to bis-N-methylacridinium nitrate (lucigenin) and NADH in accordance with the procedures of Example 1 and maintained at about room temperature for from 0 to about 80 minutes. Emitted energy was detected in accordance with the procedures of Example 1 immediately after exposure of the cells to probe and probe-trigger. The results of those studies are summarized in FIG. 7.

Figure 7:
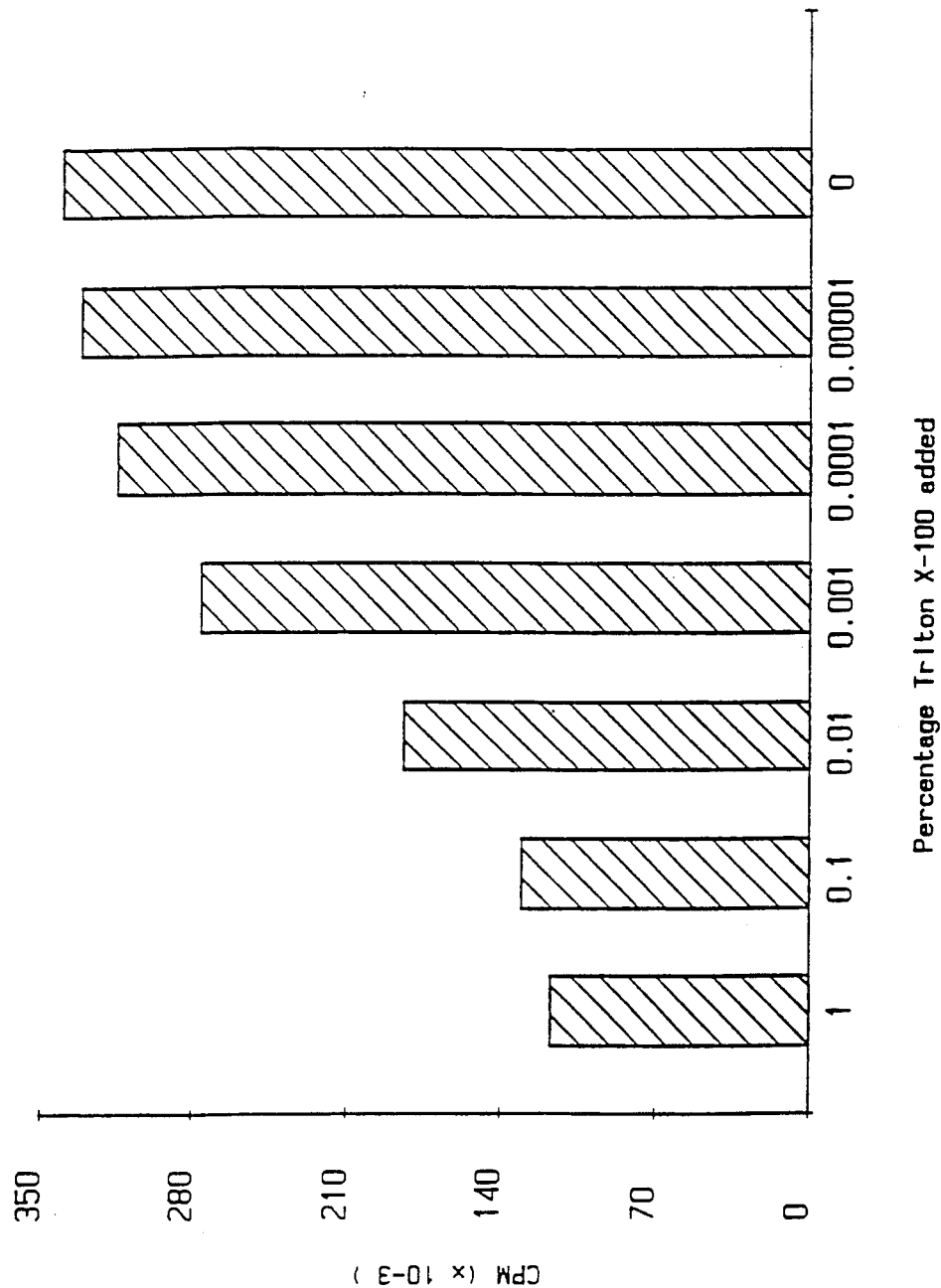
FIG. 7 shows the effect of Triton X-100 on the chemiluminescence (CPM) observed with 50,000 K562 cells, immediately after the addition of a probe, probe-trigger solution.

The data in FIG. 7 show that a process of the present invention can be used to assay cytotoxicity.

EXAMPLE 4

Cell Differentiation Assay

Hemoglobin producing cells, ATCC K562 were obtained from and suspended in RPMI medium. Cells were plated into individual wells of a 96 well microtiter plate at a concentration of 10 cells/well and cultured for four days in the absence and presence of varying concentrations of 3'-azido-3'-deoxythymidine (AZT) or PMEA. Both AZT and PMEA are known to stimulate differentiation of such hemoglobin producing cells. After culturing, cells were exposed to bis-N-methylacridinium nitrate (lucigenin) and NADH in accordance with the procedures of Example 1 and maintained at about room temperature for from 0 to about 80 minutes. Emitted energy was detected in accordance with the procedures of Example 1 immediately after exposure of the cells to probe and probe-trigger. The results of those studies are summarized in FIG. 8.

Figure 8:
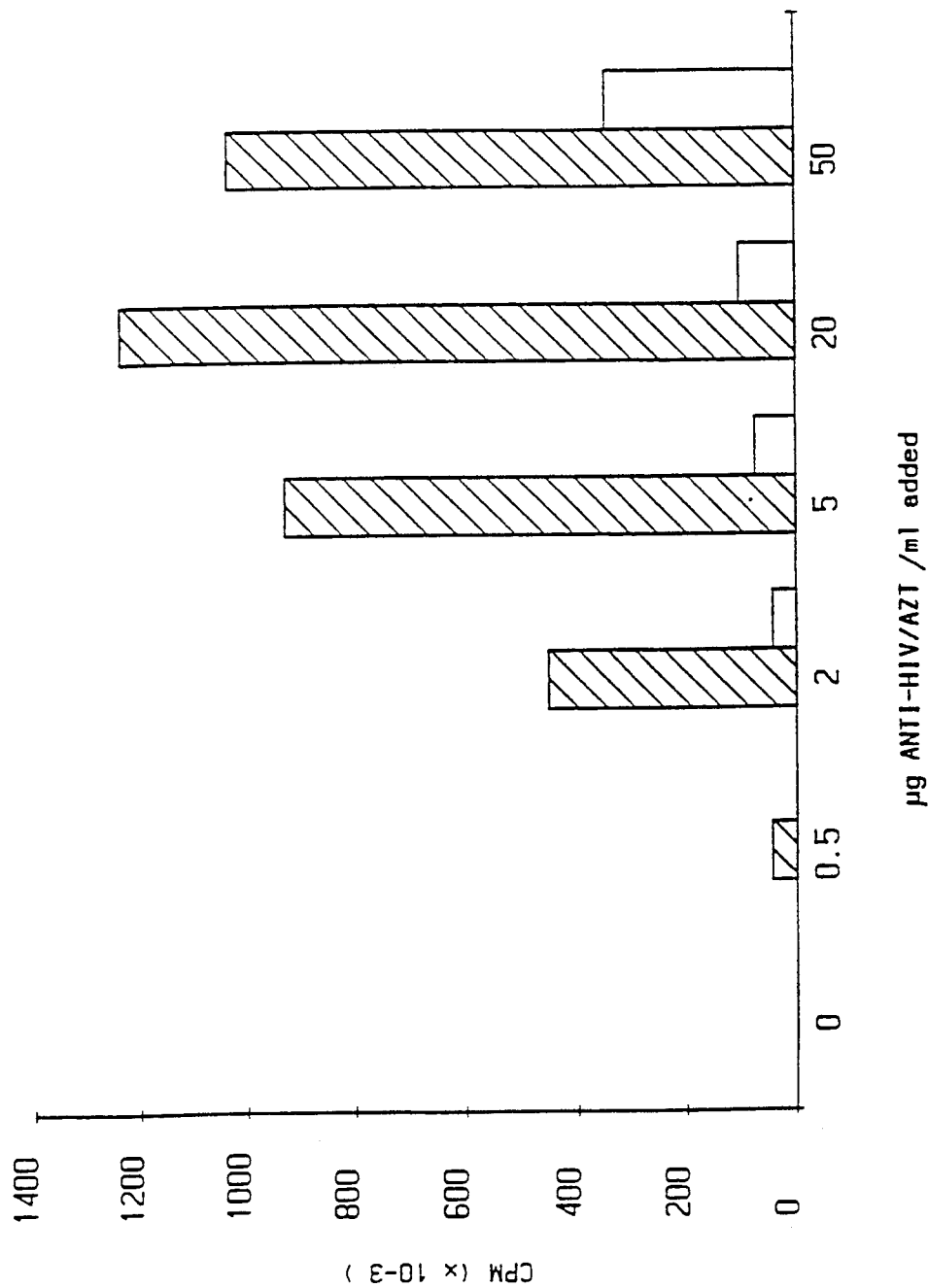
FIG. 8 shows chemiluminescence (CPM) of the differentiation of hemoglobin producing cells, grown in the presence of AZT and an experimental anti-HIV drug (empty blocks=AZT).

The data in FIG. 8 show that a process of the present invention can be used to assay cell differentiation.

The foregoing examples illustrate particular embodiments of the present invention. One of ordinary skill in the art will readily appreciate that changes, modifications and alterations to those embodiments can be made without departing from the scope and true spirit of the present invention.

I claim:

1. A process of quantifying the number of viable cells in an aqueous suspension of cells, which process comprises the steps of:
    a) admixing an effective detection amount of a light-emitting non-hazardous probe with said suspension to form an admixture, wherein the emission of light from said probe is proportional to and activated by an amount of a stimulant;
    b) exposing said admixture to an effective triggering amount of a probe-trigger, wherein said probe-trigger interacts with said viable cells to generate said stimulant in an amount proportional to the number of said viable cells;
    c) maintaining said admixture under biological reaction conditions and for a period of time sufficient for activation of said light-emitting non-hazardous probe; and
    d) detecting the amount of light emitted from said probe and correlating said amount of light to the number of viable cells.

2. The process according to claim 1 wherein said light-emitting non-hazardous probe is a chemiluminogenic probe or an otherwise luminescent probe.

3. The process according to claim 2 wherein said chemiluminogenic probe is lucigenin, lophine, luminol, a dioxetane or an acridinium salt.

4. The process according to claim 1 wherein said stimulant is an unstable oxygen derived species.

5. The process according to claim 4 wherein said unstable oxygen derived species is singlet oxygen, a superoxide radical, a hydroxyl radical, hydrogen peroxide or a protonated superoxide radical.

6. The process according to claim 1 wherein said probe-trigger is a reduced form of a coenzyme for an oxidation-reduction reaction.

7. The process according to claim 6 wherein said form of a coenzyme is reduced nicotinamide adenine dinucleotide (NADH), reduced nicotinamide adenine dinucleotide phosphate (NADPH), reduced flavin mononucleotide (FMNH), or reduced flavin adenine dinucleotide (FADH).

8. The process according to claim 1 wherein said aqueous suspension comprises a mixture of acetone and water.

9. The process according to claim 1 wherein said viable cells are freeze-dried cells.

10. A process of quantifying the number of negatively charged particles in an aqueous suspension, which process comprises the steps of:
   a) admixing an effective detection amount of a cationic, light-emitting non-hazardous probe with said suspension to form an admixture, wherein said probe binds to said particles and the emission of light from said probe is proportional to and activated by an amount of a stimulant;
   b) exposing said admixture to an effective triggering amount of a probe-trigger, wherein said probe-trigger interacts with said negatively charged particles to generate said stimulant in an amount proportional to the number of said particles;
   c) maintaining said admixture under chemical reaction conditions and for a period of time sufficient for activation of said light-emitting non-hazardous probe; and
   d) detecting the amount of light emitted from said probe and correlating said amount of light to the number of negatively charged particles.

11. The process according to claim 10 wherein said light-emitting non-hazardous probe is a chemiluminogenic probe or an otherwise luminescent probe.

12. The process according to claim 11 wherein said chemiluminogenic probe is lucigenin, lophine, luminol, a dioxetane or an acridinium salt.

13. The process according to claim 10 wherein said stimulant is an unstable oxygen derived species.

14. The process according to claim 13 wherein said unstable oxygen derived species is singlet oxygen, a superoxide radical, a hydroxyl radical, hydrogen peroxide or a protonated superoxide radical.

15. The process according to claim 10 wherein said probe-trigger is a reduced form of a coenzyme for an oxidation-reduction reaction.

16. The process according to claim 15 wherein said form of a coenzyme is reduced nicotinamide adenine dinucleotide (NADH), reduced nicotinamide adenine dinucleotide phosphate (NADPH), reduced flavin mononucleotide (FMNH), or reduced flavin adenine dinucleotide (FADH).

17. The process according to claim 10 wherein said aqueous suspension comprises a mixture of acetone and water.

18. A process of quantifying the number of viable cells in an aqueous suspension of said cells, which process comprises the steps of:
   a) admixing an effective detection amount of a chemiluminogenic probe with said suspension to form an admixture, wherein the emission of light from said chemiluminogenic probe is proportional to and activated by an amount of an unstable oxygen derived species;
   b) exposing said admixture to an amount of reduced nicotinamide adenine dinucleotide (NADH) or reduced nicotinamide adenine dinucleotide phosphate (NADPH) wherein the amount of NADH or NADPH is sufficient to stimulate detectable emitted light from said probe
   c) maintaining said admixture under biological reaction conditions and for a period of time sufficient for activation of said chemiluminogenic probe; and
   d) detecting the amount of light emitted from said chemiluminogenic probe and correlating said amount of light to the number of viable cells.

19. The process according to claim 18 wherein an effective detection amount of said chemiluminogenic probe is from about $10^{-10}$ to about $10^{-3}$M.

20. The process according to claim 18 wherein said chemiluminogenic probe is lucigenin, lophine, luminol, a dioxetane or an acridinium salt.

21. The process according to claim 18 wherein said unstable oxygen derived species is singlet oxygen, a superoxide radical, a hydroxyl radical, hydrogen peroxide or a protonated superoxide radical.

22. The process according to claim 18 wherein said period of time is less than about 30 minutes.

23. The process according to claim 18 wherein said period of time is less than about 10 minutes to about 20 minutes.

24. A cell toxicity assay comprising the steps of:
   a) admixing an effective detection amount of a light-emitting non-hazardous probe with an aqueous suspension of cells to form an admixture, wherein the emission of light from said probe is proportional to and activated by an amount of a stimulant;
   b) exposing said admixture to a frist effective triggering amount of a first probe-trigger, wherein said first probe-trigger interacts with viable cells in said suspension to generate said stimulant in an amount proportional to the number of said viable cells;
   c) maintaining said admixture under biological reaction conditions and for a period of time sufficient for activation of said light-emitting non-hazardous probe;
   d) detecting the emission of light from said light-emitting probe;
   e) contacting said admixture with a suspected toxin;
   f) re-exposing said admixture to a second effective triggering amount of a second probe-trigger, wherein said second probe-trigger interacts with said viable cells to generate said stimulant in an amount proportional to the number of said viable cells;
   g) maintaining said admixture under biological reaction conditions and for a period of time sufficient for activation of said light-emitting non-hazardous probe;
   h) detecting the emission of light from said probe; and
   i) comparing the detected emission of light from step (d) with the detected emission of light from step (h) and thereby determining the effect of the suspected toxin.

25. The process according to claim 24 wherein said first and second probe triggers are the same.

26. The process according to claim 24 wherein said light-emitting non-hazardous probe is a chemiluminogenic probe or an otherwise luminescent probe.

27. The process according to claim 26 wherein said chemiluminogenic probe is lucigenin, lophine, luminol, a dioxetane or an acridinium salt.

28. The process according to claim 24 wherein said stimulant is an unstable oxygen derived species.

29. The process according to claim 28 wherein said unstable oxygen derived species is singlet oxygen, a superoxide radical, a hydroxyl radical, hydrogen peroxide or a protonated superoxide radical.

30. The process according to claim 24 wherein said first and second probe-triggers are a reduced form of a coenzyme for an oxidation-reduction reaction.

31. The process according to claim 30 wherein said form of a coenzyme is reduced nicotinamide adenine dinucleotide (NADH), reduced nicotinamide adenine dinucleotide phosphate (NADPH), reduced flavin mononucleotide (FMNH), or reduced flavin adenine dinucleotide (FADH).

32. A cell proliferation assay comprising the steps of:
  a) admixing an effective detection amount of a light-emitting non-hazardous probe with an aqueous suspension of cells to form an admixture, wherein the emission of light energy from said probe is proportional to and activated by an amount of a stimulant;
  b) exposing said admixture to a first effective triggering amount of a first probe-trigger, wherein said first probe-trigger interacts with viable cells in said suspension to generate said stimulant in an amount proportional to the number of said viable cells;
  c) maintaining said admixture under biological reaction conditions and for a period of time sufficient for activation of said light-emitting non-hazardous probe;
  d) detecting the emission of light-energy from said probe;
  e) contacting said admixture to a suspected cell proliferation stimulant;
  f) re-exposing said admixture to a second effective triggering amount of a second probe-trigger, wherein said second probe-trigger interacts with said viable cells to generate said stimulant in an amount proportional to the number of viable cells;
  g) maintaining said admixture under biological reaction conditions and for a period of time sufficient for activation of said light-emitting non-hazardous probe;
  h) detecting the emission of light-energy from said probe; and
  i) comparing the detected emission of light-energy from step (d) with the detected emission of light from step (h) and thereby determining the effect of the suspected cell proliferation agent.

33. The process according to claim 32 wherein said first and second probe triggers are the same.

34. The process according to claim 32 wherein said light-emitting non-hazardous probe is a chemiluminogenic probe or an otherwise luminescent probe.

35. The process according to claim 34 wherein said chemiluminogenic probe is lucigenin, lophine, luminol, a dioxetane or an acridinium salt.

36. The process according to claim 32 wherein said stimulant is an unstable oxygen derived species.

37. The process according to claim 36 wherein said unstable oxygen derived species is singlet oxygen, a superoxide radical, a hydroxyl radical, hydrogen peroxide or a protonated superoxide radical.

38. The process according to claim 32 wherein said first and second probe triggers are a reduced form of a coenzyme for an oxidation-reduction reaction.

39. The process according to claim 38 wherein said form of a coenzyme is reduced nicotinamide adenine dinucleotide (NADH), reduced nicotinamide adenine dinucleotide phosphate (NADPH), reduced flavin mononucleotide (FMNH), or reduced flavin adenine dinucleotide (FADH).

40. A cell differentiation assay comprising the steps of:
  a) admixing an effective detection amount of an light-emitting non-hazardous probe with an aqueous suspension of cells to form an admixture, wherein the emission of light energy from said probe is proportional to and activated by an amount of a stimulant;
  b) exposing said admixture to a first effective triggering amount of a first probe-trigger, wherein said first probe-trigger interacts with said cells to generate said stimulant in an amount proportional to the number of said cells;
  c) maintaining said admixture under biological reaction conditions and for a period of time sufficient for activation of said light-emitting non-hazardous probe;
  d) detecting the emission of light-energy from said probe;
  e) contacting said admixture to a suspected cell differentiation stimulant;
  f) re-exposing said admixture to a second effective triggering amount of a second probe-trigger, wherein said second probe-trigger interacts with said cells in an active metabolic state to generate said stimulant in an amount proportional to the number of said cells;
  g) maintaining said admixture under biological reaction conditions and for a period of time sufficient for activation of said light-emitting non-hazardous probe;
  h) detecting the emission of light-energy from said probe; and
  i) comparing the detected emission of light from step (d) with the detected emission of light from step (h) and thereby determining the effect of the suspected cell differentiation stimulant.

41. The process according to claim 40 wherein said first and second probe triggers are the same.

42. The process according to claim 40 wherein said light-emitting non-hazardous probe is a chemiluminogenic probe or an otherwise luminescent probe.

43. The process according to claim 42 wherein said chemiluminogenic probe is lucigenin, lophine, luminol, a dioxetane or an acridinium salt.

44. The process according to claim 40 wherein said stimulant is an unstable oxygen derived species.

45. The process according to claim 44 wherein said unstable oxygen derived species is singlet oxygen, a superoxide radical, a hydroxyl radical, hydrogen peroxide or a protonated superoxide radical.

46. The process according to claim 40 wherein said first and second probe triggers are a reduced form of a coenzyme for an oxidation-reduction reaction.

47. The process according to claim 46 wherein said form of a coenzyme is reduced nicotinamide adenine dinucleotide (NADH), reduced nicotinamide adenine dinucleotide phosphate (NADPH), reduced flavin mononucleotide (FMNH), or reduced flavin adenine dinucleotide (FADH).

* * * * *